US010426600B2

(12) United States Patent
Coleman et al.

(10) Patent No.: US 10,426,600 B2
(45) Date of Patent: Oct. 1, 2019

(54) ACCOMMODATING INTRAOCULAR LENS AND METHODS OF USE

(75) Inventors: D. Jackson Coleman, Howorth, NJ (US); Adrian Glasser, Bellaire, TX (US)

(73) Assignees: University of Houston, Houston, TX (US); Cornell Research Foundation, Inc., Ithaca, NY (US)

( * ) Notice: Subject to any disclaimer, the term of this patent is extended or adjusted under 35 U.S.C. 154(b) by 1457 days.

(21) Appl. No.: 11/572,061

(22) PCT Filed: Jul. 21, 2005

(86) PCT No.: PCT/US2005/025748
§ 371 (c)(1),
(2), (4) Date: May 5, 2008

(87) PCT Pub. No.: WO2006/014738
PCT Pub. Date: Feb. 9, 2006

(65) Prior Publication Data
US 2008/0221676 A1    Sep. 11, 2008

Related U.S. Application Data

(60) Provisional application No. 60/590,078, filed on Jul. 22, 2004.

(51) Int. Cl.
*A61F 2/16*    (2006.01)

(52) U.S. Cl.
CPC ............ *A61F 2/1635* (2013.01); *A61F 2/164* (2015.04); *A61F 2/1643* (2015.04); *A61F 2/1648* (2013.01); *A61F 2002/169* (2015.04); *A61F 2002/1682* (2015.04); *A61F 2002/16902* (2015.04); *A61F 2250/0024* (2013.01)

(58) Field of Classification Search
CPC .... A61F 2/1635; A61F 2/1648; A61F 2/1643; A61F 2/164; A61F 2002/1682; A61F 2002/169; A61F 2002/16901; A61F 2002/16902
USPC .................................................. 623/4.1, 6.11
See application file for complete search history.

(56) References Cited

U.S. PATENT DOCUMENTS

| | | | |
|---|---|---|---|
| 4,435,856 A * | 3/1984 | L'Esperance | ................ 623/6.34 |
| 5,674,282 A | 10/1997 | Cumming | |
| 5,964,802 A * | 10/1999 | Anello | .................. A61F 2/1613 623/6.4 |
| 6,277,146 B1 | 8/2001 | Peyman et al. | |
| 6,342,073 B1 | 1/2002 | Cumming et al. | |

(Continued)

*Primary Examiner* — Leslie Lopez
(74) *Attorney, Agent, or Firm* — Bond, Schoeneck & King, PLLC; Blaine Bettinger; William Greener (57) ABSTRACT

The present invention relates to a first intraocular lens (120) embodiment having a retainer plate (124) with an annular region surrounding a central opening and an optical lens (122) removably attached to the retainer plate within the central opening. Also disclosed is a second intraocular lens embodiment having a retainer plate with a porous or perforated annular region surrounding a central opening. An optical lens (122) is integral with the retainer plate (124) within the central opening. Methods of implanting these intraocular lens (120) embodiments into a patient's eye are disclosed. Also described here are methods of replacing the first intraocular lens embodiment after it has been implanted in a patient's eye.

17 Claims, 7 Drawing Sheets

(56) References Cited

U.S. PATENT DOCUMENTS

| | | | |
|---|---|---|---|
| 6,387,126 B1 | 5/2002 | Cumming | |
| 6,451,056 B1 | 9/2002 | Cumming | |
| 6,749,634 B2 * | 6/2004 | Hanna | 623/6.37 |
| 6,755,858 B1 | 6/2004 | White | |
| 7,435,258 B2 | 10/2008 | Blake | |
| 2003/0050696 A1 | 3/2003 | Cumming | |
| 2003/0060877 A1 * | 3/2003 | Falotico et al. | 623/1.42 |
| 2004/0148022 A1 * | 7/2004 | Eggleston | A61F 2/16 623/6.22 |
| 2006/0064161 A1 | 3/2006 | Blake | |
| 2006/0100704 A1 | 5/2006 | Blake et al. | |
| 2006/0116765 A1 | 6/2006 | Blake et al. | |

\* cited by examiner

ACCOMMODATING INTRAOCULAR LENS AND METHODS OF USE

This application claims the priority benefit of U.S. Provisional Patent Application Ser. No. 60/590,078, filed Jul. 22, 2004, which is hereby incorporated by reference in its entirety.

FIELD OF THE INVENTION

This invention relates to intraocular lenses, methods of implanting intraocular lenses into a patient's eye, and methods of replacing intraocular lenses that have been implanted into a patient's eye.

BACKGROUND OF THE INVENTION

Cataracts are currently the leading cause of blindness among adults in the United States. A cataract is a clouding of a part of the eye known as the crystalline lens. Although cataracts result from many conditions, the most frequent cause is the natural aging process. Most people develop some clouding of the lens after the age of 60. About 50 percent of Americans ages 65 to 74 have cataract, and about 70 percent of those age 75 and over have it. As there are growing numbers of elderly in the United States, the incidence of cataracts is increasing. Other causes of cataracts may include injury, chronic eye disease, and other system-wide diseases such as, diabetes.

Surgery to remove the diseased crystalline lens is the only effective treatment for cataract. Neither diet nor medications have been shown to stop cataract formation. Cataract surgery is now a frequently performed operation in most parts of the world. More than 1.5 million cataract procedures are performed every year, and, in the majority of those cases, the diseased tissue is replaced with an artificial device known as an intraocular lens implant. This surgery is very successful in restoring vision—more than 95 percent of people who have a cataract removed have no complications and end up with better vision. Many people report not only better vision but also a reduction in the power of their lens prescription and improvements in their overall quality of life after the operation.

Presbyopia, a condition in which the natural lens of the eye becomes thicker and less flexible, is also a symptom of the natural aging process. Patients of presbyopia generally lose the ability of ocular focus due to lack of accommodation ability of the natural lens. Replacement of the natural crystalline lens with an artificial intraocular lens is an emerging treatment for patients with presbyopia.

Intraocular lenses for cataract lens replacement surgery and presbyopia correction surgery differ widely in their physical appearance and arrangement. Intraocular lenses have been described in U.S. Pat. Nos. 4,254,509, 4,298,996, 4,409,691, 4,424,597, 4,573,998, 4,664,666, 4,673,406, 4,738,680, 4,753,655, 4,778,463, 4,813,955, 4,840,627, 4,842,601, 4,963,148, 4,994,082, 5,047,051, 5,674,282, 6,342,073, 6,387,126, 6,451,056, and U.S. Patent Application Publication No. 2003/0050696.

Two general classes of intraocular lenses—accommodating and non-accommodating—have been developed. Non-accommodating intraocular lenses cannot change shape or move in the eye and, therefore, do not operate in conjunction with the natural accommodation capabilities of the human eye, whereas accommodating lenses do have at least some capability to operate in conjunction with the natural accommodation capabilities of the eye. Accommodation involves relaxation and constriction of the ciliary muscle by the brain to provide the eye with near and distant vision. This ciliary muscle action is automatic and shapes the natural crystalline lens to the appropriate optical configuration for focusing on the retina the light rays entering the eye from the scene being viewed. Ocular mechanics of natural eye accommodation are also governed by zonular ligaments connecting the ciliary muscle to the perimeter of the lens and vitreous material that fills the posterior segment of the eye.

Most non-accommodating intraocular lenses have single focus optics which focus the eye at a certain fixed distance only. Other non-accommodating lenses have bifocal optics which image both near and distant objects on the retina of the eye. The brain selects the appropriate image and suppresses the other image, so that a bifocal intraocular lens provides both near vision and distant vision without eyeglasses. Bifocal intraocular lenses, however, suffer from the disadvantage that each bifocal image represents only about 40% of the available light, and a remaining 20% of the light is lost in scatter.

A common design feature of the available accommodative intraocular lenses is to translate the optic forward in the eye. For example, the accommodating intraocular lens disclosed by U.S. Pat. No. 5,674,282 to Cumming is made of a lens body having a central optical zone or optic and plate haptics extending from diametrically opposite edges of the optic. Ciliary muscle contraction exerts opposing endwise compression forces on the ends of the lens haptics with resultant endwise compression of the lens. Relaxation of the ciliarly muscle causes retraction of the lens. Accommodating intraocular lenses designed to translate the optic forward in the eye fail to address an important feature of natural lens accommodation. That is, natural accommodation benefits considerably from changes in surface curvatures. Available accommodating intraocular lenses fail to possess the capability of undergoing changes in surface curvature. In other words, available accommodating intraocular lenses do not uniformly flex and move or maintain their flexibility with in-growth of fibroblasts around the supporting capsular structure of the eye. Furthermore, available accommodating intraocular lenses are not amenable to removal or replacement of the optical lens because of adhesion of the lens to the capsular/zonular support structure of the eye.

The present invention is directed to overcoming these and other limitations in the art.

SUMMARY OF THE INVENTION

One aspect of the present invention relates to an intraocular lens having a retainer plate with an annular region surrounding a central opening and an optical lens removably attached to the retainer plate within the central opening.

Another aspect of the present invention relates to a method of implanting an intraocular lens into a patient's eye. This method involves providing an intraocular lens having a retainer plate with an annular region surrounding a central opening and an optical lens removably attached to the retainer plate within the central opening. The intraocular lens is implanted into the patient's eye.

A further aspect of the present invention relates to a method of replacing an intraocular lens that has been implanted into a patient's eye. This method involves removing the intraocular lens from the patient's eye. The intraocular lens has a retainer plate with an annular region surrounding a central opening and a first optical lens removably attached to the retainer plate within the central opening. The first optical lens is removed from the retainer plate. A second optical lens is attached to the retainer plate within the central opening. The intraocular lens with the second optical lens is implanted into the patient's eye.

Yet another aspect of the present invention relates to an intraocular lens having a retainer plate with an annular region surrounding a central opening, where the annular region is porous or perforated, and an optical lens integral with the retainer plate within the central opening.

Still another aspect of the present invention relates to a method of implanting an intraocular lens into a patient's eye. This method involves providing an intraocular lens having a retainer plate with an annular region surrounding a central opening, where the annular region is porous or perforated, and an optical lens integral with the retainer plate within the central opening. The intraocular lens is implanted into the patient's eye.

The present invention provides an improved accommodating intraocular lens, which is suitable for replacement of the natural crystalline lens of the eye. In particular, the intraocular lens provides natural accommodation benefits, which include adjustments in surface curvatures. This is accomplished by constructing the intraocular lens of a flexible material which is porous. In addition, a removable optical lens portion permits exchange, as well as variations in aspheric lens power or cylinder alignment for optimal acuity. By having a separate retainer plate and optical lens, the inventory of optimal lens plate size and optic power allows proper sizing for both globe size and dioptic lens power. The intraocular lens of the present invention also is designed to retard fibrous in-growth, thereby keeping a clear central area for optimal acuity.

DETAILED DESCRIPTION OF THE INVENTION

One aspect of the present invention relates to an intraocular lens having a retainer plate with an annular region surrounding a central opening and an optical lens removably attached to the retainer plate within the central opening.

Figure 1:
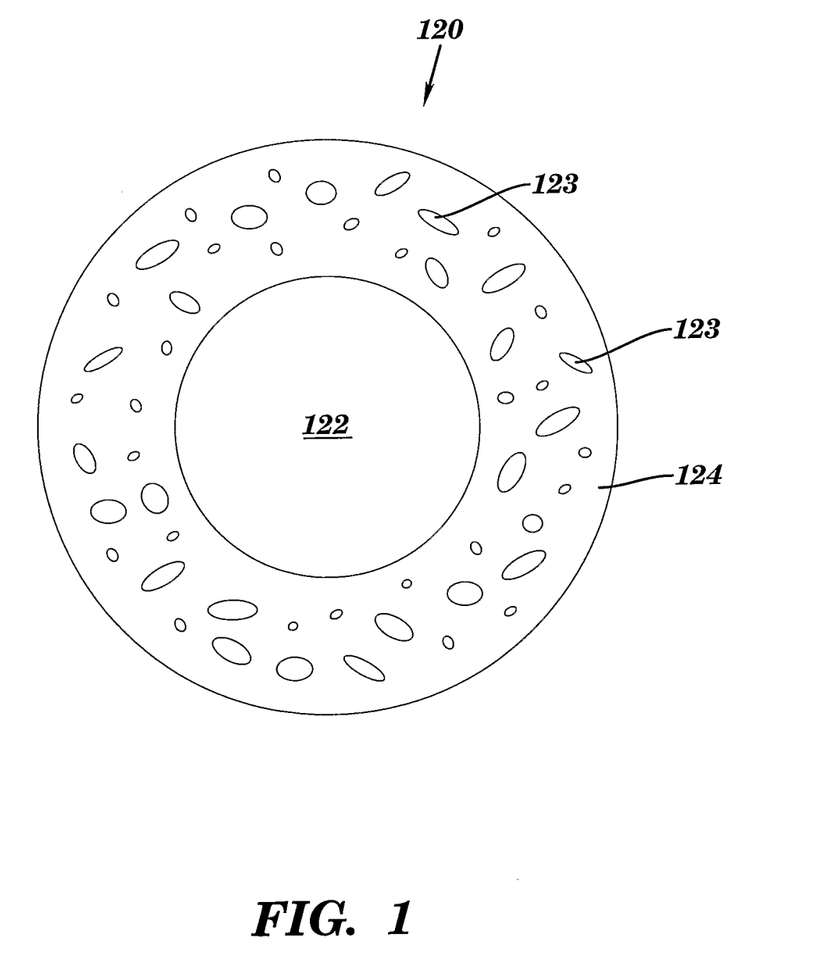
FIG. 1 is a plan view of a first embodiment of the intraocular lens of the present invention.

FIG. 1 is a plan view of the intraocular lens of the present invention. Intraocular lens 120 has optical lens 122, which is removably attached to retainer plate 124. Either or both of optical lens 122 and retainer plate 124 are constructed of a flexible material including, without limitation, acrylic, silicone, or poly(methyl methacrylate) ("PMMA"), or mixtures thereof. Flexible material allows accommodation of the intraocular lens by flexing with ciliary muscle contraction and vitreous pressure. As a result, intraocular lens 120 has the ability to adjust to surface curvatures. The optical power of a lens or a surface is determined to some extent by the curvature of the surface. An increase or steepening of the curvature (a decrease in the radius of curvature) will result in an increase in the optical power. An optic which can flex to increase the curvature of one or both surfaces (decrease the radius of curvature) will undergo an increase in optical power. The intraocular lens of the present invention allows the optic to undergo a change in one or both surface curvatures to undergo an increase in optical power.

Retainer plate 124 is preferably fenestrated, or is porous or perforated. Such pores 123 are depicted in FIG. 1. Fenestrated retainer plate 124 enables optical lens 122 to remain relatively undistorted when force is applied at one or more locations on retainer plate 124 as a result of accommodation pressures. In addition to its accommodation capabilities, retainer plate 124 also functions to inhibit fibrous growth by creating a mote surrounding optical lens 122. The diameter of retainer plate 124 may vary, depending upon the size and shape of the patient's eye. Typically, the outer diameter of retainer plate 124 is from about 8 mm to about 15 mm.

Optical lens 122 of intraocular lens 120 is also preferably constructed of a flexible material as described supra to allow accommodation by flexing with ciliary muscle contraction and permit changes is surface curvature. Optical lens 122 may take on a variety of shapes and sizes. For example, optical lens 122 may be spherical, aspherical, or cylindrical. The shape and size of optical lens 122 is at least partially dependent upon the optical needs of the patient. The diameter of optical lens 122 may vary, depending upon the size and shape of the patient's eye, as well as the patient's optical needs. Typically, the diameter of optical lens 122 is from about 4 mm to about 6.5 mm.

Figure 2:
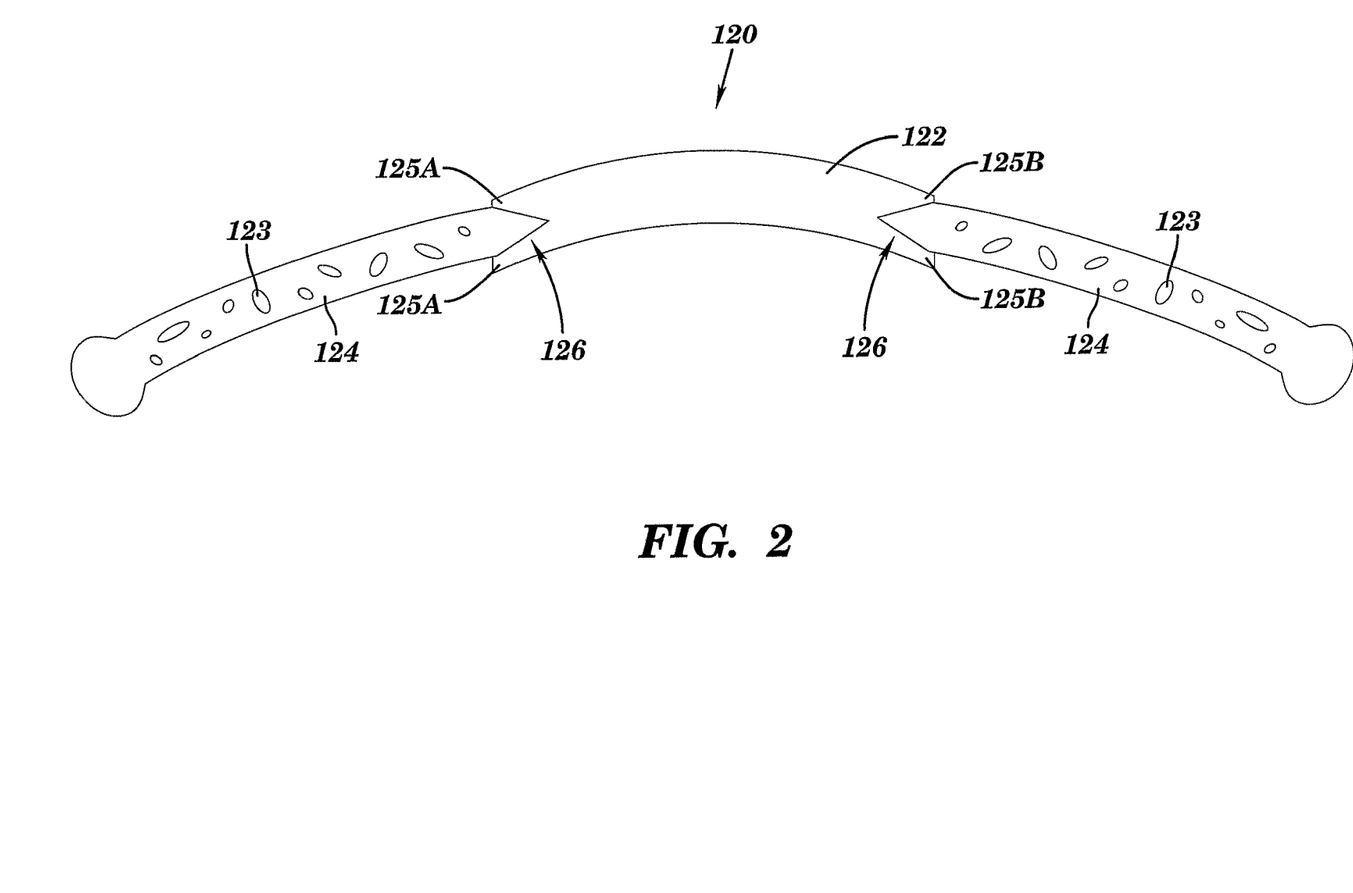
FIG. 2 is a cross-sectional side view of one embodiment of the intraocular lens of FIG. 1, in which the optical lens is removably attached to the retainer plate by providing the optical lens with an annular groove into which the retainer plate fits.
Figure 3:
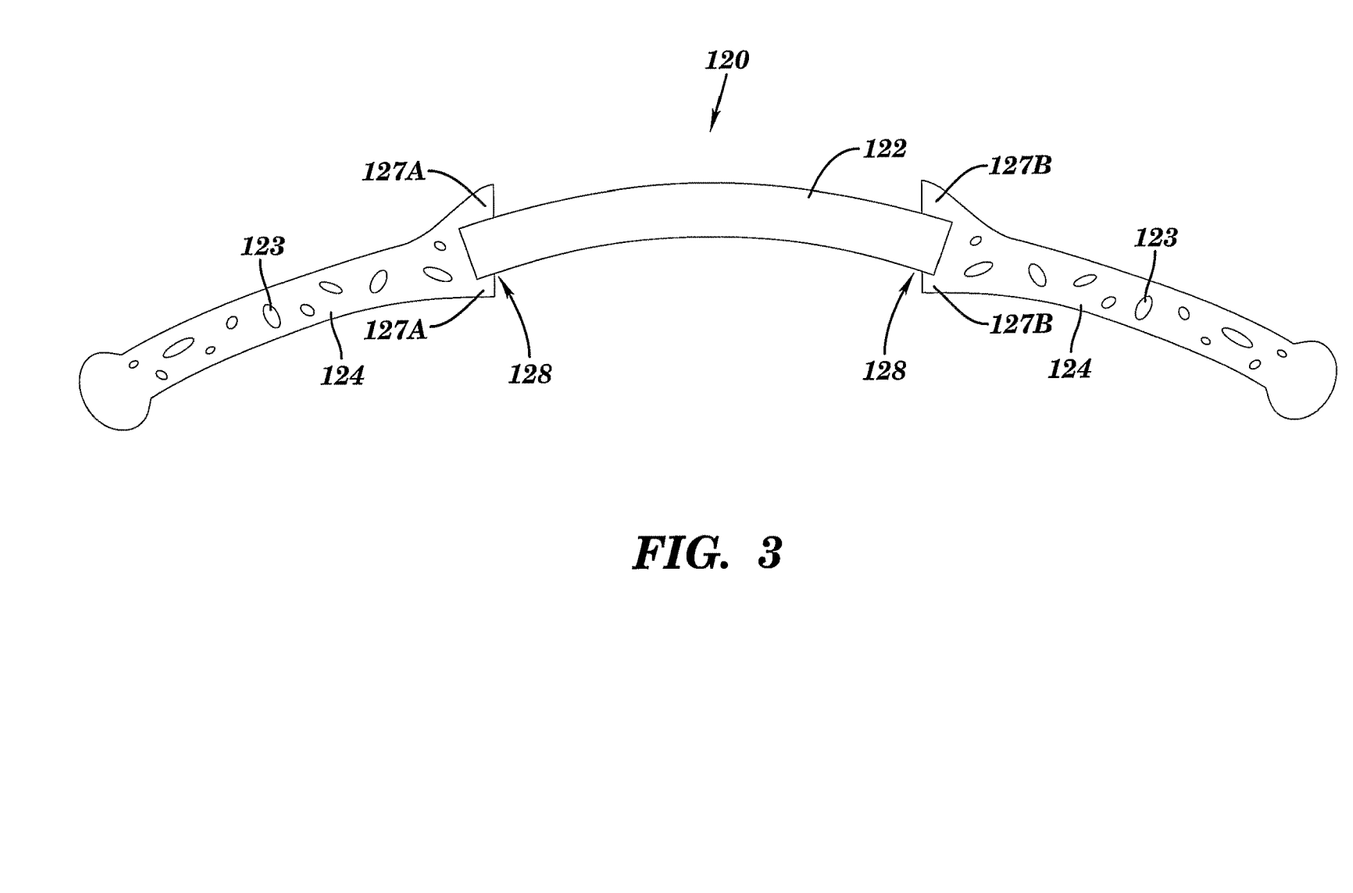
FIG. 3 is a cross-sectional side view of a second embodiment of the intraocular lens of FIG. 1, in which the optical lens is removably attached to the retainer plate by providing the retainer plate with an annular groove into which the optical lens fits.
Figure 4A:
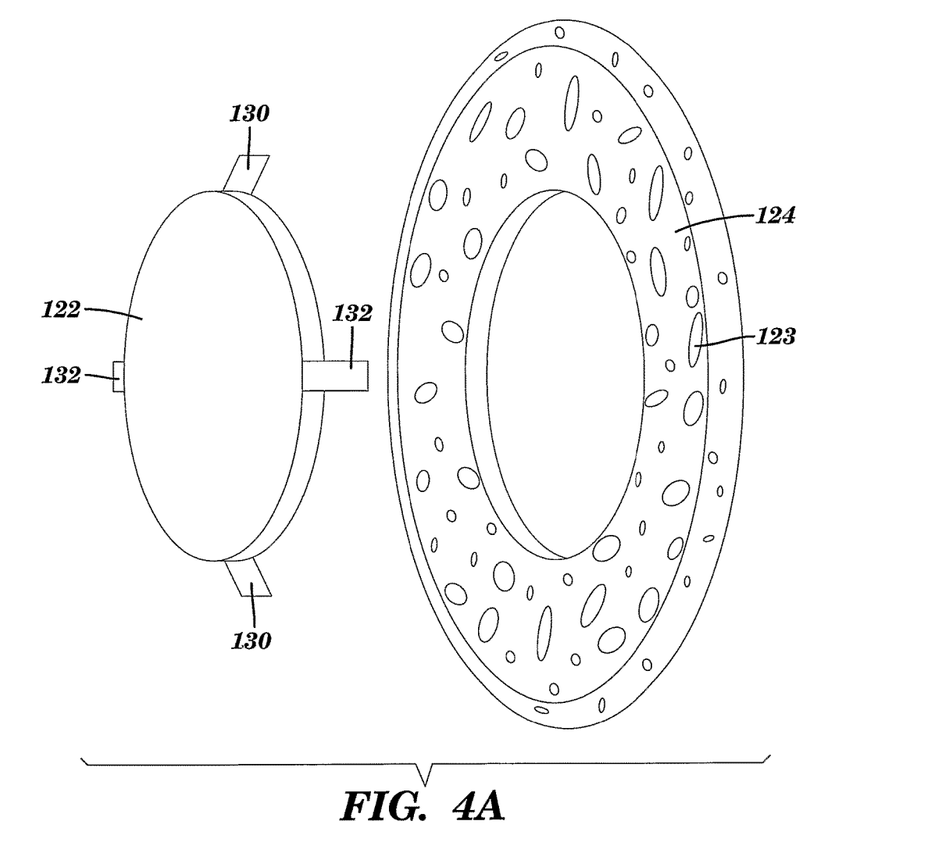
FIG. 4A is an exploded, perspective view of the intraocular lens of FIG. 1, in which the optical lens has flanges on its anterior surface to prevent posterior displacement when the optical lens is removably attached to the retainer plate. The optical lens also has flanges on its posterior surface to prevent anterior displacement when the optical lens is removably attached to the retainer plate.
Figure 4B:
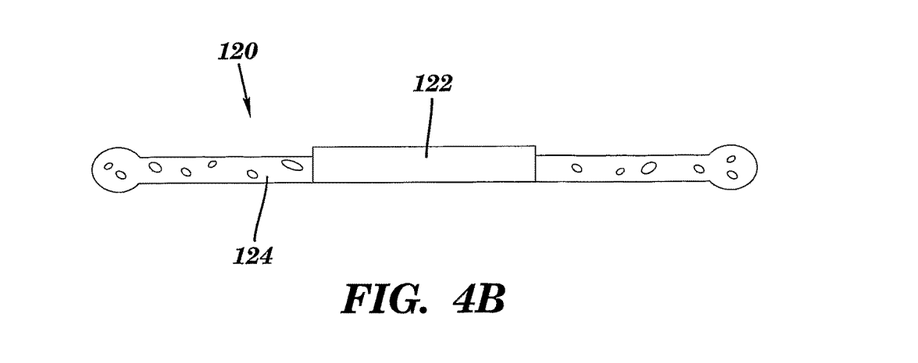
FIG. 4B is a cross-sectional side view of the intraocular lens of FIG. 4A.

Optical lens 122 may be attached to retainer plate 124 by a variety of designs. Exemplary attachment designs include, but are not limited to, those illustrated in FIGS. 2-4. In FIG. 2, optical lens 122 has annular groove 126, defined by fingers 125A and 125B, into which retainer plate 124 fits. FIG. 3 illustrates an alternative attachment of optical lens 122 to retainer plate 124 in which retainer plate 124 has annular groove 128, defined by fingers 127A and 127B, into which optical lens 122 fits. In FIGS. 4A-B, optical lens 122 is attached to retainer plate 124 by anterior flanges 132 and posterior flanges 130. Anterior flanges 132 prevent posterior displacement of optical lens 122 and posterior flanges 130 prevent anterior displacement of optical lens 122. When such flanges are employed to attach optical lens 122 to retainer plate 124, optical lens 122 protrudes from the plane defined by retainer plate 124, as shown in FIG. 4B, to prevent fibrous growth on optical lens 122.

The intraocular lens of the present invention can be provided with a medication. Suitable medications include, without limitation, antifibroplastic agents, cyclosporine, and mitomycin.

A further aspect of the present invention relates to a method of implanting an intraocular lens into a patient's eye. This method involves providing an intraocular lens having a retainer plate with an annular region surrounding a central opening and an optical lens removably attached to the retainer plate within the central opening. The intraocular lens is implanted into the patient's eye.

The surgical procedures for implanting an accommodating intraocular lens into a patient's eye are discussed in great detail in U.S. Pat. No. 5,674,282 to Cumming, which is hereby incorporated by reference in its entirety.

Figure 5:
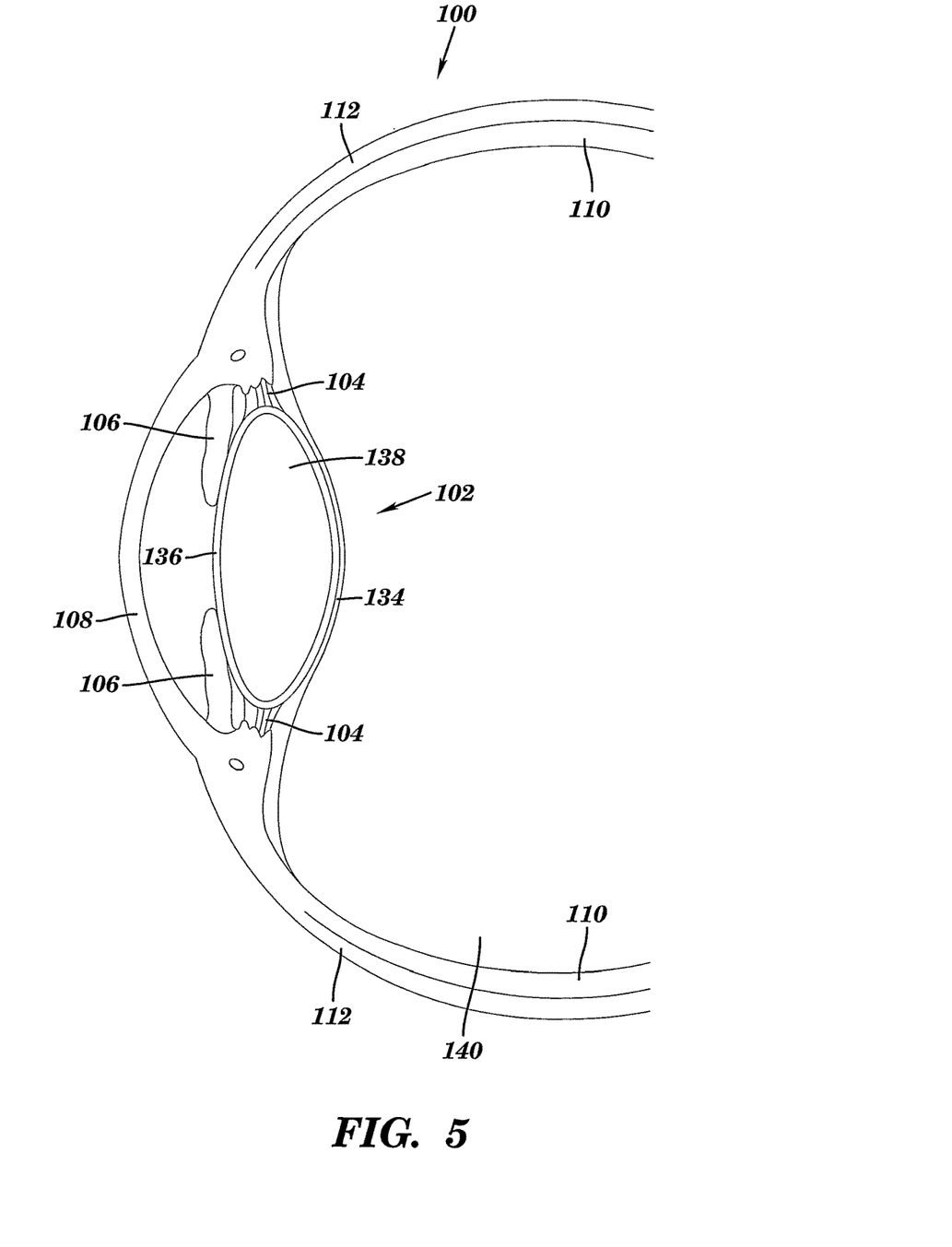
FIG. 5 is a cross-section of a human eye, showing the positioning and attachment of the natural crystalline lens.

FIG. 5 illustrates a cross-sectional view of a human eye. Human eye 100 has natural crystalline lens 102. Lens 102 is contained in a capsule having anterior wall 136 and posterior wall 134, also known as anterior and posterior capsules. Anterior wall 136 and posterior wall 134 contain crystalline lens matrix 138, which in its normal state is clear, and in its cataract stage is cloudy. Prior to implanting an intraocular lens of the present invention into a patient's eye, lens matrix 138 must be removed. Surgical implantation of an intraocular lens therefore involves removing and replacing lens matrix 138 with an artificial intraocular lens.

Figure 6:
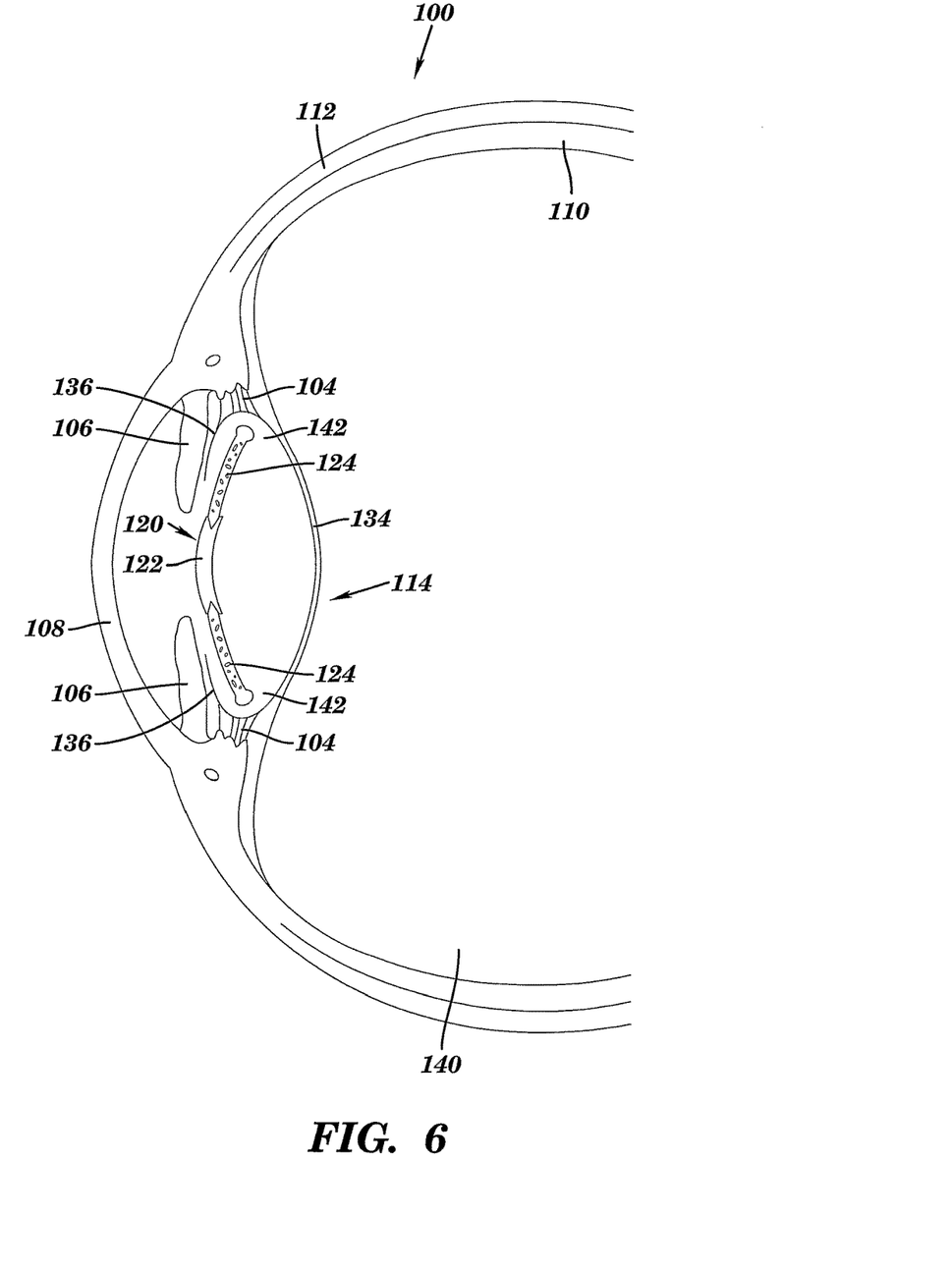
FIG. 6 is a cross-section of a human eye in which the natural crystalline lens has been removed and an intraocular lens of the present invention has been surgically implanted.

Replacement of a crystalline lens with an intraocular lens generally requires surgery in which anterior wall 136 is torn along a circular tear line, or capsulorhexis, in the center of anterior wall 136. Lens matrix 138 is removed through the capsulotomy. FIG. 6 shows a cross-section of eye 100 after lens matrix 138 has been removed. Anterior cornea 108, opaque sclera 112, retina 110, iris 106, and vitreous cavity 140 remain in eye 100. Capsular bag 114 is what is left from removal of lens matrix 138, and it remains intact within the eye. A remnant of anterior wall 136 remains after removal of lens matrix 138 as annular anterior capsular rim 136 (FIG. 6). Posterior wall 134 is joined to anterior capsular rim 136 along the perimeter of capsular bag 114 to form annular crevice-like capsular bag sulcus 142 between rim 136 and posterior wall 134. Capsular bag 114 is secured about its perimeter to the ciliary muscle of the eye by zonular ligaments 104.

FIG. 6 shows implantation of intraocular lens 120 into eye 100. Intraocular lens 120 is implanted within capsular bag 114, such that retainer plate 124 resides, at least partially, within capsular bag sulcus 142 between rim 136 and posterior wall 134. During the post-operative healing period following surgical implantation of intraocular lens 120, epithelial cells under rim 136 of capsular bag 114 cause fusion of rim 136 to posterior wall 134 by fibrosis. Fibrosis embeds retainer plate 124 within capsular bag 114, and thereby holds intraocular lens 120 in place. By implanting intraocular lens 120 into the remnants of capsular bag 114, it benefits from the accommodation forces of the eye as would a natural lens, including ciliary muscle action, zonular, and vitreous flexing. As such, intraocular lens 120 is able to make adjustments which facilitate focusing on far and near objects. Given the improved features of the intraocular lens of the present invention, including construction with flexible material and a fenestrated retainer plate, it also has the accommodation ability of surface curvature.

Implantation of the intraocular lens of the present invention may be carried out by attaching the optical lens to the retainer plate while the optical lens and the retainer plate are in the patient's eye. The retainer plate may first be inserted into the capsule and then the optical lens is inserted into the capsule, or visa versa. Preferably, the retainer plate is folded prior to insertion into the capsule. Inserting the retainer plate into the capsule may be carried out by rolling the retainer plate and inserting it into the capsular bag through a finite diameter (3-4 mm) injector. After the retainer plate and optical lens have been inserted into the eye, the optical lens may be attached to the retainer plate in the capsule of the eye.

In a preferred embodiment, a medication as described supra is applied to the intraocular lens prior to implanting the intraocular lens into the patient's eye.

Prior to implantation into a patient's eye, the intraocular lens of the present invention can be custom designed or fit for the physical dimensions and/or optical needs of the patient. Thus, retainer plate 124 is selected to fit the physical dimensions of the patient's eye by selecting a suitable diameter. Likewise, optical lens 122 is selected to fit the optical needs of the patient's eye as well as the particular retainer plate selected to fit the patient's physical dimensions.

Upon selecting the appropriate retainer plate and optical lens, optical lens 122 is attached to retainer plate 124 within the central opening of retainer plate 124 prior to implantation. Intraocular lens 120 is then implanted into the patient's eye. Depending upon the particular embodiment of the intraocular lens of the present invention, the optical lens is attached to the retainer plate by providing the optical lens with an annular groove into which the retainer plate fits, by providing the retainer plate with an annular groove into which the optical lens fits, or by securing the optical lens to the retainer plate by flanges attached to the anterior and posterior surfaces of the optical lens. See FIGS. 2-4.

After intraocular lens 120 is implanted into the patient's eye, it may later be desirable to remove optical lens 122 from retainer plate 124 and replace it with a new optical lens. For example, removal of the optical lens may have special implications for pediatric cases where the power of the optical lens can be periodically adjusted as the patient ages and the eye grows. Thus, the methods of the present invention further relate to a method of removing an optical lens from the retainer plate after the intraocular lens has been implanted into the patient's eye and attaching a replacement optical lens to the retainer plate within the central opening while the intraocular lens is in the patient's eye.

A further aspect of the present invention relates to a method of replacing an intraocular lens that has been implanted into a patient's eye. This method involves removing the intraocular lens from the patient's eye, the intraocular lens having a retainer plate with an annular region surrounding a central opening and a first optical lens removably attached to the retainer plate within the central opening. The first optical lens is removed from the retainer plate. A second optical lens is attached to the retainer plate within the central opening. The intraocular lens with the second optical lens is implanted into the patient's eye.

In carrying out this method, it is preferable to select the second optical lens to fit the optical needs of the patient's eye prior to attaching the second optical lens to the retainer plate. Furthermore, it is desirable to apply a medication as described supra to the second optical lens prior to implanting the intraocular lens with the second optical lens into the patient's eye.

The patient may be any mammal, such as, without limitation, horses, dogs, cats, rabbits, and small rodents. Other mammals such as pigs, sheep, cows, and other livestock may also be patients for purposes of the present invention. In a preferred embodiment, the patient is human.

Another aspect of the present invention relates to an intraocular lens having a retainer plate with an annular region surrounding a central opening, wherein the annular region is porous or perforated, and an optical lens integral with the retainer plate within the central opening.

Figure 7A:
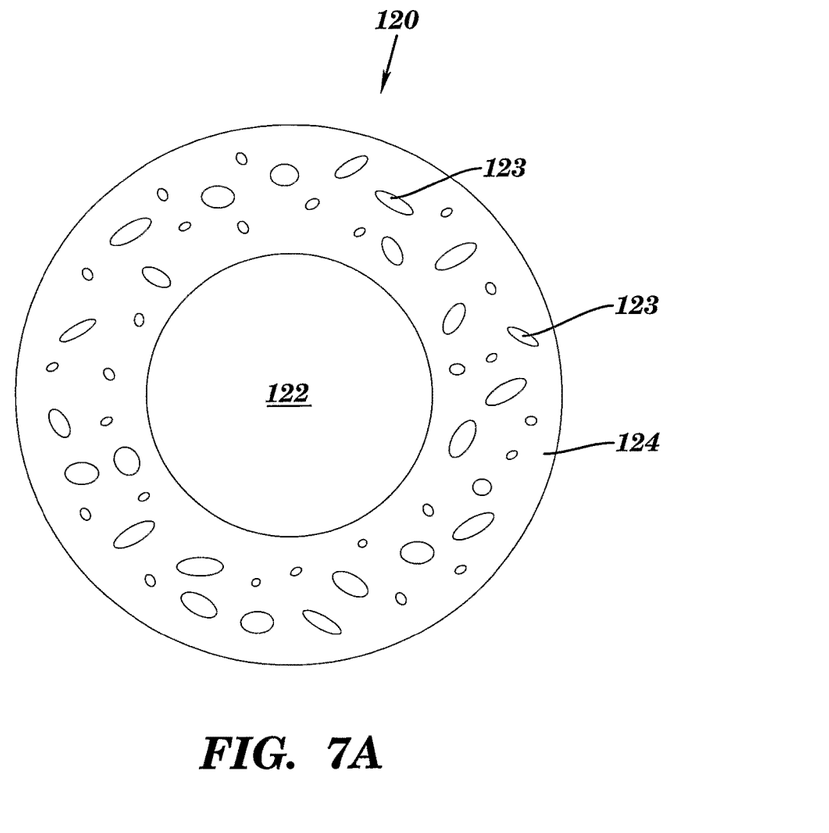
FIG. 7A is a plan view of a second embodiment of the intraocular lens of the present invention in which the porous retainer plate and the optical lens are integral.
Figure 7B:
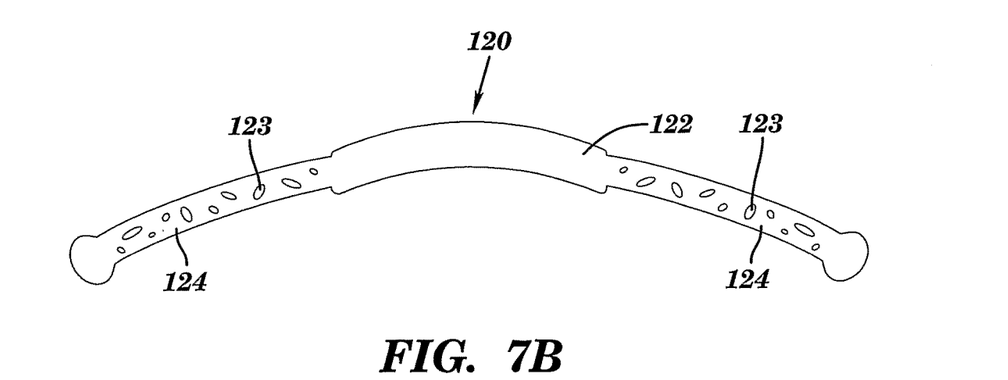
FIG. 7B is a cross-sectional view of the intraocular lens of FIG. 7A.

FIGS. 7A and 7B depict intraocular lens 120 having retainer plate 124, which has pores 123. Optical lens 122 is integral with retainer plate 124. Preferably, retainer plate 124 and optical lens 122 are made from a single piece of material. Suitable materials for construction of intraocular lens 120 are discussed supra.

Yet another aspect of the present invention relates to a method of implanting an intraocular lens into a patient's eye. This method involves providing an intraocular lens having a retainer plate with an annular region surrounding a central opening, wherein the annular region is porous or perforated, and an optical lens integral with the retainer plate within the central opening. The intraocular lens is implanted into the patient's eye.

The same procedures described supra apply to carrying out this method of the present invention.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. An accommodating intraocular lens (IOL) comprising:
a flexible retainer plate consisting of a material annular region surrounding a central aperture having a diameter,
wherein the annular region has an inner surface defining the diameter of the central aperture,
characterized by a flexibility that is sufficient to allow a continuous accommodating movement of the IOL; and
an optical element consisting of a single optical lens having an anterior surface and a posterior surface, disposed fully within the aperture, and at least one of one or more flanges on the anterior surface to prevent posterior displacement and one or more flanges on the posterior surface to prevent anterior displacement.

2. The intraocular lens according to claim 1, wherein either or both of the retainer plate and the optical lens are comprised of a material selected from the group consisting of acrylic, silicone, and PMMA.

3. The intraocular lens according to claim 1, wherein the retainer plate is porous or perforated.

4. The intraocular lens according to claim 1, wherein the optical lens is spherical.

5. The intraocular lens according to claim 1, wherein the optical lens is aspherical.

6. The intraocular lens according to claim 1, wherein the optical lens is cylindrical.

7. The intraocular lens according to claim 1, wherein the optical lens is flexible.

8. An accommodating intraocular lens (IOL) comprising:
a flexible retainer plate consisting of a material annular region surrounding a central aperture having a diameter, wherein the annular region has an inner surface defining the diameter of the central aperture, characterized by a flexibility that is sufficient to allow a continuous accommodating movement of the IOL; and
an optical element consisting of a single optical lens having an anterior surface and a posterior surface disposed fully within the aperture,
wherein at least one of: a) the optical lens has a groove around at least a portion of its periphery and at least a corresponding portion of the inner surface of the annular region of the retainer plate has a shape adapted to engage with the groove portion of the lens and b) the retainer plate has a groove in at least a portion of the inner surface of the annular region and at least a corresponding portion of the periphery of the lens has a shape adapted to engage with the groove portion of the inner surface of the annular region of the retainer plate.

9. The intraocular lens according to claim 1, wherein the retainer plate and optical lens are provided with a medication.

10. The intraocular lens according to claim 9, wherein the medication is selected from the group consisting of antifibroplastic agents, cyclosporin, and mitomycin.

11. The intraocular lens according to claim 8, wherein either or both of the retainer plate and the optical lens are comprised of a material selected from the group consisting of acrylic, silicone, and PMMA.

12. The intraocular lens according to claim 8, wherein the retainer plate is porous or perforated.

13. The intraocular lens according to claim 8, wherein the optical lens is spherical.

14. The intraocular lens according to claim 8, wherein the optical lens is aspherical.

15. The intraocular lens according to claim 8, wherein the optical lens is cylindrical.

16. The intraocular lens according to claim 8, wherein the retainer plate and optical lens are provided with a medication.

17. The intraocular lens according to claim 16, wherein the medication is selected from the group consisting of antifibroplastic agents, cyclosporin, and mitomycin.

* * * * *